United States Patent [19]

Fukuda et al.

[11] Patent Number: 4,698,304

[45] Date of Patent: Oct. 6, 1987

[54] METHOD FOR PRODUCING HYDROCARBON MIXTURES

[75] Inventors: Hideo Fukuda, Osaka; Takahira Ogawa; Takao Fujii, both of Kumamoto, all of Japan

[73] Assignee: Hideo Fukuda, Osaka, Japan

[21] Appl. No.: 785,479

[22] Filed: Oct. 8, 1985

[30] Foreign Application Priority Data

Oct. 9, 1984 [JP] Japan .................................. 59-211972

[51] Int. Cl.$^4$ ........................... C12P 5/00; C12P 5/02
[52] U.S. Cl. ................................... 435/166; 435/167; 435/807
[58] Field of Search ..................... 435/166, 167, 807

[56] References Cited

FOREIGN PATENT DOCUMENTS

| | | | |
|---|---|---|---|
| 133597 | 2/1985 | European Pat. Off. ............ | 435/167 |
| 198983 | 11/1984 | Japan .................................. | 435/166 |

OTHER PUBLICATIONS

Lynch, *Nature* vol. 240, Nov. 3, 1972, pp. 45–46.
Graham et al, Canadian J. of Microbiology, vol. 26, pp. 1340–1347 (1980).
Davis, "Detection of Microbially Produced Gaseous Hydrocarbons Other than Methane." Science 119 pp. 381–382 (1954).
Gollakota et al, "Biogas (Natural Gas) Production by Anaerobic Digestion of Oil Cake by a Mixed Culture Isolated . . . " Biochemical and Biophysical Research Communications 110(1) pp. 32–35 (1983).
Illag et al, "Production of Ethylene by Fungi" Science 159 pp. 1357–1358 (1968).
Primrose, "Formation of Ethylene by *Escherichia Coli*" Journal of General Microbiology 95 pp. 159–165 (1976).
Primrose, "Ethylene-Forming Bacteria from Soil and Water" Journal of General Microbiology 97 pp. 343–346 (1976).

*Primary Examiner*—John E. Tarcza
*Attorney, Agent, or Firm*—Burgess, Ryan and Wayne

[57] ABSTRACT

Mixtures of saturated or unsaturated $C_2$–$C_5$ hydrocarbons are produced by aerobically cultivating a microorganism belonging to a wide variety of genera Fungi, Yeasts, Bacteria and Actinomycetes in a water-containing medium, and recovering the hydrocarbon mixtures from the liquid phase or/and gaseous ambience of the medium. Industrial wastes and various biomass can be employed as nutrient sources in the cultivation.

6 Claims, No Drawings

METHOD FOR PRODUCING HYDROCARBON MIXTURES

The present invention relates to a microbial method of producing hydrocarbon mixtures.

According to the present invention, there can be produced hydrocarbons, for example, a saturated hydrocarbon such as ethane, propane, n-butane, isobutane, n-pentane and isopentane etc., and an unsaturated hydrocarbon such as ethylene, propylene, 1-butene, isobutene, trans-2-butene and cis-2-butene etc. as a mixture containing at least two kinds of hydrocarbons by means of microorganisms. These hydrocarbons occur in petroleum cracking product gases and natural gases, and have been made available from various stages of their purification and fractionation. However, the terrestrial reserves of these materials are limited.

Regarding the formation of ethane by microorganisms, there are reports in relation to a culture employing bovine feces or digested sludge as well as microorganisms grown on the surface of an agar medium [J. B. Davis and R. M. Squires; Science, 119, 381–382 (1954)], settled sludge in San Francisco Bay [R. S. Oremland; Appl. Environment. Microbiol., 42, 122–129 (1981)], and mushrooms [E. M. Turner; J. Gen. Microbiol.; 91, 167–176 (1975)]. However, these reports are no more than exploratory in nature, and almost no definite mention has been made of the type of ethane-producing microorganisms involved.

Regarding the production of ethylene by microorganisms, there have been several reports, for example, an exploratory investigation of 228 fungi species [L, Ilag, and Roy W/.Curtis; Science, 159, 1357–1358 (1968)], studies on microorganisms of the genus Mucor and on *Aspergillus clavatus* [J. M. Lynch, and S. H. Harper; J. Gen. Microbiol. 80, 187–195 (1974)], exploratory studies on soil bacteria [S. B. Primrose; J. Gen. Microbiol. 97, 343–346 (1976)], studies on *Escherichia coli* and Pseudomanas species [S. B. Primrose; J. Gen. Microbiol. 95, 159–165 (1976); S. B. Primrose and Dilworth; J. Gen. Microbiol. H. T. Freebairn and I. W. Budenhagen; Nature, 202, 313–314 (1964)], a study on *Saccharomyces cerevisiae* [K. C. Thomas and M. Spencer; Can. J. Microbiol. 23, 1669–1674)], a study on mushrooms [E. M. Turner; j. Gen. Microbiol. 91, 167–176 (1975)], and a comprehensive review of such literatures [M. Lieberman; Ann. Rev. Plant Physiol. 30, 533–591 (1979)]. However, the majority of these reports are no more than exploratory in nature, and no definite mention has been made of the types of ethylene-producing microorganisms involved.

Regarding the production of propane, propylene, butane and butene by microorganisms, there is a report that methane as well as trace amount of ethane, propane, butane (chemical structures not established) and butene (chemical structures not established) were detected when a mixture of microorganisms in fermented bovine feces (strains not isolated or identified) was anaerobically cultivated [K. G. Gollakota and B. Jayalakshmi; Biochemical and Biophysical Research Communications, 110, 32–35 (1983)], a report that small amounts of ethane, ethylene, propane, propylene, and n-butane were formed by mushrooms [E. M. turner, M. Wright, T. Ward, and D. J. Osborne; J. Gen. Microbiol., 91, 167–176 (1975)], and a report that small amounts of ethane, ethylene, propane and propylene were detected in anaerobic methane fermentation with a mixture of microorganisms contained in bovine feces (strains not isolated or identified) and on agar plate culture of *Penicillium digitatum* ATCC 10030 [J. B. Davis and R. M. Squires; Science, 119, 381–382 (1954)]. However, according to these reports, the yields of hydrocarbons are invariably small, the processes are either anaerobic culture or solid surface culture, and either the microorganisms involved are indefinite or the chemical structure of product hydrocarbons are not identified.

In any of the above prior reports, the yield of hydrocarbons of not less than $C_2$ is small and anaerobic culture or solid culture employed in the reports is not suitable for industrial large scale production.

Furthermore, because there is no clear description of the species of the microorganisms, the reports have insufficient reproduceability.

The present inventors have conducted research to find a method for producing mixtures of hydrocarbons having at least carbon number $C_2$ by means of microorganisms with sufficient reproduceability and conceived the present invention.

The present invention is directed to a method for producing a hydrocarbon mixture which comprises cultivating aerobically a strain of microorganism capable of producing simultaneously at least two kinds of saturated or unsaturated $C_2$–$C_5$ hydrocarbons in a water-containing medium to thereby cause the formation of said hydrocarbons in the liquid phase and/or the gaseous ambience of the medium, and recovering said hydrocarbons as a mixture from said liquid phase and/or gaseous ambience.

As the microorganisms which can be employed in accordance with the present invention, there may be exemplified fungi belonging to the genera Saprolegnia, Phytophthora, Mucor, Rhizopus, Absidia, Mortierella, Cunninghamella, Taphrina, Monascus, Nectria, Gibberella, Chaetomium, Neurospora, Geotrichum, Monilia, Trichoderma, Aspergillus, Penicillium, Paecilomyces, Gliocladium, Sporotrichum, Microsporum, Trichophyton, Cladosporium, Syncephalastrum, Phycomyces and Eupenicillium, inclusive of mutant strains thereof; yeast belonging to the genera Endomyces, Shizosaccharomyces, Pichia, Hansenula, Debaryomyces, Saccharomycopsis, Rhodotorula, Sporobolomyces, Cryptococcus, Candida, and Brettanomyces, inclusive of mutant strains thereof; bacteria belonging to the genera Bacillus, Brevibacterium, Corynebacterium, Flavobacterium, Klebsiella, Micrococcus, Mycoplana, Paracoccus, Proteus, Pseudomanas, Salmonella, Serratia, and Acetobacter, inclusive of mutant strains thereof; and actinomycetes belonging to the genera Streptomyces, Actinomyces and Intrasporangium, inclusive of mutant strains thereof.

Of these microorganisms, the following strains are representative of the organisms capable of producing $C_2$–$C_5$ hydrocarbons in substantial quantities.

FUNGI: *Saprolegnia parasitica* IFO-8978, *Phytophtora capsici* IFO-8386, *Mucor hiemalis* f. corticolus IFO-9401, *Mucor hiemalis* f. luteus IFO-9411, *Rhizopus delemar* IFO-4801, *Rhizopus formosaensis* IFO-4732, *Rhizopus javanicus* IFO-5441, *Rhizopus japonicus* IFO-4758, IFO-4780, IFO-5318, IFO-5319, *Rhizopus niveus* IFO-4759, *Rhizopus oryzae* IFO-4705, *Rhizopus stolonifer* IFO-5411, *Absidia cylindrospora* IFO-4000, *Mortierella isabellina* IFO-8183, *Mortierella elongata* IFO-8570, *Cunninghamella elegans* IFO-4441, *Taphrina Caerulescens* IFO-9242, *Taphrina wiesneri* IFO-7776, *Monascus anka* IFO-6540, *Monascus albidus* IFO-4489, *Nectria*

*flammea* IFO-9628, *Gibberella fujikuroi* IFO-5268, *Chaetomium globosum* IFO-6347, *Neurospora crassa* IFO-6067, *Geotrichum candidum* IFO-4597, *Monilia geophila* IFO-5425, *Trichoderma viride* IFO-4847, *Aspergillus clavatus* IFO-4045, IFO-8606, *Penicillium digitatum* IFO-7758, *Paecilomyces carneus* IFO-8292, *Paecilomyces elegans* IFO-6619, *Gliocladium aureum* IFO-9055, *Gliocladium deliquescens* IFO-7062, *Gliocladium roseum* IFO-7063, *Sporotrichum aureum* IFO-9381, *Microsporum gypseum* IFO-5948, *Microsporum cookei* IFO-7862, *Trichophyton mentagrophytes* IFO-5466, *Cladosporium resinae* IFO-8588, *Syncephalastrum racemosum* IFO-4816, *Phycomyces nitens* IFO-9422, *Eupenicillium lapidosum* IFO-6100, IFO-9700, IFO-9701 etc., YEASTS: *Endomyces geotrichum* IFO-9541, *Endomyces reessii* IFO-1112, *Endomyces magnusii* IFO-0110, *Schizosaccharomyces octosporus* IFO-0353, *Schizosaccharomyces pombe* IFO-0340, *Saccharomyces bailii* IFO-0468, *Saccharomyces* sp. IFO-2363, IFO-2266, IFO-2112, IFO-2115, IFO-2242, IFO-2343, IFO-2344, IFO-2345, IFO-2346, IFO-2347 and IFO-2376, *Pichia membranaefaciens* IFO-0181, *Pichia acaciae* IFO-1681, *Pichia besseyi* IFO-1707, *Pichia farinosa* IFO-0459, *Hansenula capsulata* IFO-0721, *Debaryomyces nepalensis* IFO-1428, *Saccharomycopsis lipolytica* IFO-1658, *Saccharomycopsis crataegensis* IFO-1708, *Saccharomycopsis fibuligera* IFO-1745, *Rhodotorula glutinis* IFO-0697, IFO-1501, *Rhodotorula minuta* IFO-0387, IFO-1435, *Rhodotorula minuta* var. *texensis* IFO-0879, IFO-0932, IFO-1006 and IFO-1102, *Rhodotorula marina* IFO-1421, *Sporobolomyces salmonicolor* IFO-0374, *Sporobolomyces pararoseus* IFO-0376, *Cryptococcus albidus* IFO-0378, IFO-0434, IFO-0939, IFO-1044 and IFO-1320, *Cryptococcus flavus* IFO-0407, *Cryptococcus laurentii* var. *flavescens* IFO-0384, *Cryptococcus luteolus* IFO-0411, *Candida albicans* IFO-1060, *Candida butyri* IFO-1571, *Cnadida guilliermondii* IFO-0454, *Brttanomyces bruxellensis* IFO-0628, *Brttanomyces intermedius* IFO-1587 etc., BACTERIA: *Bacillus circulans* IFO-3329, *Bacillus coagulans* IFO-3557, *Bacillus pumilus* IFO-3813, *Bacillus subtilis* IFO-3023, *Brevibacterium ammoniagenes* ATCC-6872, *Brevibacterium lactofermentum* ATCC-13655, *Corynebacterium aquaticum* IFO-12154, *Corynebacterium fascians* IFO-12077, *Corynebacterium paurometabolum* IFO-12160, *Flavobacterium capsulatum* IFO-12533, *Klebsiella pneumoniae* IFO-3317, *Micrococcus luteus* IFO-3064, *Mycrococcus roseus* IFO-3764, *Mycroplana dimorpha* IFO-13291, *Paracoccus denitrificans* IFO-12422, *Proteus mirabilis* IFO-3849, *Pseudomonas aeruginosa* IFO-3445, *Pseudomonas putida* IFO-3738, *Pseudomonas stutzeri* IFO-3773, *Salmonella typhimurium* IFO-12529, *Serratia marcescens* IFO-12648, *Acetobacter aceti* IFO-3281 etc., ACTINOMYCETES: *streptomyces flavelous* IFO-3408, *Streptomyces fradiae* IFO-3360, *Streptomyces griseus* IFO-3102, *Streptomyces lavendulae* IFO-3145, IFO-13709, *Streptomyces viridochromogenus* IFO-3113, *Streptomyces regensis* IFO-13448, *Actinomyces vulgaris* IFO-13109, *Intrasporangium calvum* IFO-12989 etc.

In addition to these strains, many strains of the genera mentioned above have been found to produce the hydrocarbon mixtures.

The culture of the strains in the present invention may be carried out employing a liquid or solid medium and, if desired, the liquid medium may be contacted with the strains fixed in a suitable carrier in the form of bioreactor.

The culture medium used for cultivation of such microorganisms may be a conventional medium for culture of fungi, yeasts, bacteria or actinomycetes, which contains carbon sources, nitrogen sources, inorganic salts, and other nutrients.

Thus, various carbohydrates such as glucose, sucrose, maltose, starch, xylose, sorbitol, etc., alcohols such as glycerol, ethanol, etc., organic acids such as acetic acid and other fatty acids, and crude materials containing them may be used as carbon sources. The main raw materials which are particularly useful for the purposes of present invention are reproducible biomass which are either naturally occurring or available artificially as by-products, such as materials from agricultural, forestal, fisheries and live-stock industry activities, industrial waste water, various industrial wastes, and active sludges from the biological treatment of public sewage, plant effluents, or excreta, etc. Though it depends on the strains of organisms used, these main materials are preliminarily dissolved, decomposed or otherwise pre-treated, if necessary. As nitrogen sources, there can be advantageously used ammonia gas, aqueous ammonia and ammonium salts.

When a biomass is used as the main raw material, the addition of such nitrogen sources may not be essential. As inorganic salts, phosphates, potassium salts, magnesium salts, sodium salts, calcium salts, etc. can be routinely employed, although these may be dispensed with when a biomass is employed.

The addition of vitamins and amino acids or of materials containing them such as yeast extract, peptone, meat extract, corn steep liquor, etc. may contribute to accelerated growth of the strain used or improved yields of desired hydrocarbon mixtures.

In particular, the addition of some kinds of amino acids and benzene compounds increase the yield of isobutane, some kinds of amino acids increase the yield of ethylene and some kinds of amino acids increase the yield of saturated hydrocarbons. The facts are explained concretely by the following test examples:

Employing culture media and conditions for yeasts and fungi indicated in Tables 1 and 2, microorganisms belonging to genera Rhodotorula, Cryprococcus and Rhizopus were cultivated and the formation rate of hydrocarbons was determined by the method below-mentioned. The results are shown in Tables 3 and 4.

TABLE 1

| Medium ingre-dients | Composition of media for each type of strain (Numerals in the Table show g/l) ||||||
|---|---|---|---|---|---|---|
| | Type of strain ||||||
| | Fungi || Yeasts || Bacteria | Actino-mycetes |
| | Kind of media ||||||
| | NB | C.D.* | NB | C.D.* | NB | NB |
| Glucose | 20 | 20 | 20 | 20 | 20 | 20 |
| Polypeptone | 5 | — | 5 | — | 5 | 5 |
| Meat extract | 3 | — | 3 | — | 3 | — |
| Ammonium sulfate | — | 3.0 | — | 5.0 | — | 2 |
| Potassium primary phosphate | — | — | — | 1.0 | — | — |
| Potassium secondary phosphate | — | 1.0 | — | — | — | — |
| Magnesium sulfate (7H$_2$O) | — | 0.5 | — | 0.5 | — | — |
| Ferrous sulfate | — | 0.01 | — | — | — | — |

TABLE 1-continued

Composition of media for each type of strain
(Numerals in the Table show g/l)

| Medium ingredients | Fungi NB | Fungi C.D.* | Yeasts NB | Yeasts C.D.* | Bacteria NB | Actinomycetes NB |
|---|---|---|---|---|---|---|
| Zinc sulfate (7H$_2$O) | — | 0.22 | — | — | — | — |
| Calcium chloride (2H$_2$O) | — | 0.1 | — | 0.1 | — | — |
| Calcium carbonate | — | — | — | 3.0 | — | — |
| Potassium chloride | — | 0.25 | — | — | — | — |
| Sodium chloride | 2 | 0.1 | 2 | 0.1 | 2 | 2 |
| Solution of inorganic salts | — | — | — | 10 ml | — | — |
| Mixed vitamin solution | — | — | — | 10 ml | — | — |
| Initial pH | 6.0 | 6.0 | 6.0 | 5.0–6.0 | 7.0 | 7.0 |

*Chemically defined media

TABLE 2

Culture conditions for each type of strain

| Culture conditions | | Fungi | Yeasts | Bacteria | Actinomycetes |
|---|---|---|---|---|---|
| Provisional culture | Temperature (°C.) | 25 | — | — | — |
| | Period (day) | 2 | — | — | — |
| Main culture | Liquid quantity [ml/ml (flask)] | 50/300 (Erlenmeyer) | 50/300 (Erlenmeyer) | 50/300 (Sakaguchi) | 50/300 (Erlenmeyer) |
| | Temperature (°C.) | 25 | 25 | 30 | 25 |
| | Shaking conditions | Rotary (dia. 7 cm, 180 rpm) | Rotary (dia. 7 cm, 180 rpm) | Recipro.* (amp.** 7 cm, 120 cpm) | Rotary (dia. 7 cm, 180 rpm) |
| | Period (day) | 4–7 | 2–3 | 1–2 | 3–7 |
| Sealed culture | Liquid quantity [ml/ml (tube)] | 1–2/34 | 1–2/34 | 1–2/34 | 1–2/34 |
| | Temperature (°C.) | 25 | 25 | 30 | 25 |
| | Shaking conditions | Recipro. (amp. 3.5 cm, 130 cpm) | Recipro. (amp. 3.5 cm, 130 cpm) | Recipro. (amp. 3.5 cm, 130 cpm) | Recipro. (amp. 3.5 cm, 130 cpm) |
| | Period (hour) | 5–10 | 5–10 | 5–10 | 5–10 |

*Reciprocatory
**amplitude

TABLE 3

Effects of additives on mixed gas formation (1)*

| Strain name | Kind of medium | Additives (1) | Additives (2) | C$_2$ ethane | C$_2$ ethylene | C$_3$ propane | C$_3$ propylene | C$_4$ iso-butane | C$_4$ n-butane | C$_4$ 1-butene | C$_4$ iso-butene | C$_4$ trans-2-butene | C$_4$ cis-2-butene | C$_5$ iso-pentane | C$_5$ n-pentane |
|---|---|---|---|---|---|---|---|---|---|---|---|---|---|---|---|
| Rhodotorula minuta IFO 1102 | NB | — | — | | 0.2 | | 0.2 | | 0.1 | | 4.3 | | | 0.1 | 0.7 |
| | C.D.** | — | — | | | | | | | | | | | | |
| | C.D. | Leu | — | | trace | | | | 0.1 | | 3.0 | | | | |
| | C.D. | Leu | Trp | | | | | | 0.1 | | 5.5 | | | | |
| | C.D. | Leu | Trp | | | | | | 0.1 | | 15.5 | | | | |
| | C.D. | Leu | Phe | | trace | | | | 0.1 | | 58.0 | | | | |
| | C.D. | Leu | Benzoic acid | | | | | | 0.1 | | 25.0 | | | | |
| | C.D. | Leu | L-Phenyl-glycine | | | | | | 0.1 | | 20.0 | | | | |
| | C.D. | Leu | L-Phenyl-piruvic acid | | | | | | 0.1 | | 32.0 | | | | |
| | C.D. | Ile | — | | | | | | | | 0.1 | 0.6 | 0.1 | | |
| | C.D. | Ile | Phe | | | | | | | | 0.1 | 1.7 | 0.2 | | |
| | C.D. | Met | — | | | 6.0 | | | | | 0.3 | | | | 0.1 |
| | C.D. | Cys | — | trace | | | 0.1 | | trace | | | | | 0.1 | 0.2 |
| Rhodotorula marina IFO 1421 | NB | — | — | | 0.1 | | 0.2 | 0.1 | | | 2.7 | | 0.1 | | |
| | C.D. | — | — | | | | | | | | | | | | |
| | C.D. | Leu | — | | | | | | | | 0.3 | | | | |
| Cryptococcus albidus IFO 0378 | NB | — | — | 0.2 | | 6.5 | 0.1 | 0.1 | 0.1 | | 0.1 | | | | |
| | C.D. | — | — | | | | | | | | | | | | |
| | C.D. | Leu | — | | | | | | | | 0.1 | | | 0.1 | |
| Cryptococcus albidus | NB | — | — | | 0.2 | | 0.1 | | | | 4.4 | | | | |
| | C.D. | — | — | | | | | | | | | | | | |
| | C.D. | Leu | — | | | | | | | | 2.5 | | | 0.2 | |

TABLE 3-continued

| | | | | | | | | | $C_4$ | | | | | $C_5$ | |
|---|---|---|---|---|---|---|---|---|---|---|---|---|---|---|---|
| | | | | $C_2$ | | $C_3$ | | iso- | | 1- | | | | iso- | |
| Strain | Kind of | Additives | | eth- | ethyl- | pro- | propyl- | bu- | n- | bu- | iso- | trans-2 | cis-2- | pen- | n- |
| name | medium | (1) | (2) | ane | ene | pane | ene | tane | butane | tene | butene | butene | butene | tane | pentane |
| IFO 1044 | | | | | | | | | | | | | | | |

*Numerals in the Table show gas formation rate (nl/ml. hr).
**Chemically defined media

TABLE 4

| | | | | | | | | | | $C_4$ | | | | $C_5$ | |
|---|---|---|---|---|---|---|---|---|---|---|---|---|---|---|---|
| | | | | $C_2$ | | $C_3$ | | | | | | | | | |
| Strain | Kind of | Additives | | eth- | ethyl- | pro- | propyl- | iso- | n- | 1- | iso- | trans-2 | cis-2- | iso- | n- |
| name | medium | (1) | (2) | ane | ene | pane | ene | butane | butane | butene | butene | butene | butene | pentane | pentane |
| Rhizopus chinensis IFO 4768 | NB | — | — | | | trace | | | | | trace | | | | trace |
| | C.D.** | — | — | | | | | | | | | | | | |
| | C.D.** | Cys | — | trace | | 0.2 | | | | | | | | trace | 0.1 |
| Rhizopus delmar IFO 4697 | NB | — | — | | | trace | | | | | 0.6 | | | trace | |
| | C.D. | — | — | | | | | | | | | | | | |
| | — | Cys | " | trace | | 0.2 | 0.1 | trace | | | | | | 0.1 | 0.2 |
| Rhizopus formosaensis IFO 4732 | NB | — | — | 0.1 | 0.1 | 0.3 | 0.1 | 0.2 | | 0.1 | | | | 0.6 | 1.5 |
| | C.D. | — | — | | | | | | | | | | | | |
| | C.D. | Cys | — | | | 0.1 | 0.1 | trace | | | | | | 0.1 | 0.1 |
| Rhizopus japonicus IFO 4758 | NB | — | — | 0.1 | 0.6 | 0.7 | 0.1 | 0.3 | | 0.2 | | | | 0.7 | 1.7 |
| | C.D. | — | — | trace | 0.1 | 0.2 | trace | trace | | | | | | 0.1 | 0.4 |
| | C.D. | Cys | — | trace | 0.1 | 2.5 | 0.1 | 0.6 | | | | | | 2.8 | 5.8 |
| Rhizopus niveus IFO 4759 | NB | — | — | 0.1 | | 0.2 | 0.1 | 0.1 | | 0.2 | | | | 0.2 | 0.4 |
| | C.D. | — | — | | | | | | | | | | | | |
| | C.D. | Cys | — | trace | | 0.2 | 0.1 | 0.1 | | | | | | 0.2 | 0.5 |
| Rhizopus oligosporus IFO 8631 | NB | — | — | | | | | | | | | | | | |
| | C.D. | — | — | | | | | | | | | | | | |
| | C.D. | Cys | — | trace | | 0.2 | | | | | | | | 0.1 | 0.1 |

*Numerals in the Table show gas formation rate (nl/ml. hr).
**Chemically defined media The test example of Table 3 shows the following facts;

(1) The addition of 1 g/l of L-leucine (abbreviated as Leu in the Table) increases the formation rate of isobutene, and further addition of an aromatic amino acid such as L-tryptophane (Trp in the Table), L-tyrosine (Tyr in the Table), L-phenylalanine (Phe in the Table), etc. increases more remarkably the formation rate of isobutene. The addition of a benzene compound such as benzoic acid, L-phenylglycine, L-phenylpyruvic acid, etc. in place of the above aromatic amino acid increases the formation rate of isobutene similarly to the aromatic amino acid.

(2) The addition of 1 g/l of L-isoleucine (Ile in the Table) increases the formation rate of trans-2-butene and cis-2-butene and further addition of 1 g/l of L-phenylalanine remarkably increases the formation rate of these hydrocarbons.

(3) The addition of 1 g/l of L-methionine (Met in the Table) increases the formation rate of ethylene.

(4) The addition of 1 g/l of L-cysteine (Cys in the Table) increases the formation rate of saturated hydrocarbons such as ethane, propane, n-butane, isobutane, n-pentane, etc. The same facts are shown by the test examples in Table 4.

Accordingly, it is shown that hydrocarbons can be converted or fermentatively converted to an ingredient of the hydrocarbons by the addition of an amino acid or other compound.

In the NB medium in Tables 3 and 4, there are contained some amounts of the above-mentioned effective additives originated from the natural ingredients of the medium such as peptone, meat extract, yeast extract etc. However, depending on the purpose, it will be necessary to supply these effective additives which may be insufficient in the medium by the addition of some other cheap natural products. As already shown in Table 2, the cultivation of the mixed hydrocarbon-producing microorganisms is carried out under aerobic conditions, for example, by aerated stirring or stationary culture, with the pH and temperature being controlled at pH 2 to 9, preferably 3.0 to 8.0, and 20° to 45° C., preferably 25° to 30° C., respectively. Thus, for each strain, he optimum pH and temperature are selected. As the cultivation is conducted for 1 to 7 days, a significant amount of mixed hydrocarbons is produced.

The content of each hydrocarbon in the mixed gases produced is assayed as follows;

A $x = 1$ to 5 ml portion of the broth in the course of cultivation or at the end of cultivation is taken into a test tube with a total volume of $V = 10$ to 50 ml and after closure with a sterile rubber stopper, the broth is incubated on a reciprocating shaker at 20° to 45° C. for $t = 1$ to 7 hours. Since the respiration rate varies with different strains, it is preferable to vary the parameters V, x and t so as to prevent oxygen deficiency during shaking.

After the reciprocal shaking, $y = 0.1$ to 2 ml of the gas is taken from the top plenum of the tube using a gas syringe and subjected to the conventional FID gas chromatography using nitrogen gas as the carrier gas, (The optimum column temperature is used according to the type of the column packing. The injection temperature is also varied accordingly.)

Preferred examples of the column packing material are Porapak Q, X-28, Bond-GC/PIC, and activated alumina, and a packing material is selected according to the type of hydrocarbon. Separately, standards of various hydrocarbons are prepared and subjected to gas chromatography under the above conditions by the same procedure to measure the retention times of the hydrocarbons on the recording paper. The calibration curves of hydrocarbons are also constructed using the standards.

Referring to the gas chromatogram of the above test gas, the retention times of the peaks on the recording paper are measured and compared with those of said standards to identify the corresponding hydrocarbons. Then, the area of the fraction corresponding to each hydrocarbon is measured and the amount $Ei^{n1}$ of the hydrocarbon is calculated by reference to the calibration curve of the standard gas.

The rate of production $pi^{n1}$/ml.hr of each hydrocarbon in the test gas can be calculated by means of the following equation. The subscript i means that it varies depending on the kind of hydrocarbon in the test gas.

$$Pi = Ei \cdot \left(\frac{V-x}{Y}\right) \cdot \frac{1}{x} \cdot \frac{1}{t}$$

The present invention has one of its characteristics in that hydrocarbons formed in the form of gaseous material can be collected, concentrated and recovered as mixed gases. For example, the mixed hydrocarbons can be obtained by absorbing the mixture onto an adsorbent having a wide range of adsorbability suitable for the purpose to remove unadsorbable impurity gases and desorbing the mixture; or by separating impurity gases by liquefaction of the gaseous material under low temperature. Or the mixed hydrocarbons can be obtained by contacting the gaseous material with aqueous strong alkali such as caustic soda to remove the carbon dioxide contained in the material as a by-product, followed by adsorption unto and desorption from the above-mentioned adsorbent.

The present invention is further characterized in that readily-available, reproducible biomass, particularly the waste resources from agricultural, forestal, fisheries and livestock industry, industrial wastes, sludges available from the biological treatment of public sewage, factory waste, or excreta can be advantageously utilized as main raw materials and that practicing the present invention is tantamount to carrying out a microbiological disposal of wastes and effluents with regard to the above-mentioned biomass employed as the main raw materials. Furthermore, the method of present invention is advantageous over the conventional methods in that the main raw material is a reproducible biomass which will never be depleted, the production is accomplished under mild conditions such as relatively low temperature and low pressure because of its being a microbiological process, and the impurity gases are mostly carbon dioxide. A result, it is easy to collect, concentrate and recover the product of hydrocarbon mixtures.

The following examples are further illustrative of present invention.

EXAMPLE 1

Fifty ml of the NB medium in Table 1 was added to a conical flask of 300 ml capacity and after steam sterilization by autoclaving at 120° C. for 15 minutes, a loopful of one of precultured strains in the case of fungi or of strains from slant culture in the other cases was inoculated to the flask which was incubated in accordance with the culture conditions indicated in Table 2.

The strains employed in the cultivation are shown in Table 5.

A 1 to 2 ml of the culture thus prepared was taken into a sterile test tube of 34 ml capacity and after hermetic closure, subjected to seal-cultivation under conditions described in Table 2 to form and accumulate mixed hydrocarbons. After the completion of the seal-cultivation, a 1 ml portion of the plenum gas was taken from each test tube with a gas syringe and subjected to gas chromatography and the formation rate of each ingredient in the gas was calculated as set forth in the foregoing. The results are shown in Table 5.

TABLE 5

Formation of hydrocarbon mixtures by each strain
[Numerals in the Table show formation rates (nl/ml/hour)]

| Genera | Species | Strains | $C_1$ methane | ethane | $C_2$ ethylene | acetylene | propane | $C_3$ propylene | iso- butane | n- butane | 1- butene | $C_4$ iso- butene | trans-2- butene | cis-2- butene | $C_5$ iso- pentane | n- pentane | remarks |
|---|---|---|---|---|---|---|---|---|---|---|---|---|---|---|---|---|---|
| | | | | | | Fungi (1) | | | | | | | | | | | |
| Saprolegnia | parasitica | IFO 8978 | | 0.4 | 4.5 | | | | | | | | | | | | |
| Phytophthora | capsici | 8386 | | | | | | | | | | | | | | | |
| Mucor | hiemalis | 9401 | | 1.9 | 7.1 | | 0.1 | | | 0.1 | | 0.2 | | | | | |
| | f. corticolus | | | | | | 0.1 | | | | | 0.1 | | | | | |
| Mucor | hiemalis | 9411 | | 1.1 | | | | | | | | 0.1 | | | | | |
| | f. luteus | | | | | | | | | | | | | | | | |
| Rhizopus | delemar | 4801 | | 0.1 | | | 0.2 | 0.1 | | 0.1 | | 0.1 | | | 0.3 | 0.3 | |
| Rhizopus | formosaensis | 4732 | | 0.1 | 0.1 | | 0.3 | 0.1 | | 0.2 | | 0.1 | | | 0.6 | 1.5 | |
| Rhizopus | javanicus | 5441 | | 0.7 | 0.1 | | 0.2 | 0.1 | | 0.2 | | 0.5 | | | 0.1 | 0.1 | |
| Rhizopus | japonicus | 4758 | | 0.1 | 0.6 | | 0.7 | 0.1 | | 0.3 | | 0.2 | | | 0.7 | 1.7 | |
| Rhizopus | japonicus | 4780 | | | | | 0.2 | 0.1 | | 0.1 | | 0.3 | | | 0.2 | 0.3 | |
| Rhizopus | japonicus | 5318 | | | | | 0.2 | 0.1 | | 0.1 | | 0.2 | | | 0.4 | 0.4 | |
| Rhizopus | niveus | 5319 | | | 0.1 | | 0.1 | 0.1 | | 0.1 | | 0.2 | | | 0.1 | 0.2 | |
| Rhizopus | oryzae | 4759 | | 0.1 | | | 0.2 | 0.1 | | 0.1 | | 0.2 | | | 0.2 | 0.4 | |
| Rhizopus | stolonifer | 4705 | | | | | 0.1 | 0.1 | | 0.1 | | 0.2 | | | 0.2 | 0.2 | |
| Rhizopus | cylindrospora | 5411 | | | | | 0.2 | 0.1 | | 0.1 | | 0.2 | | | 0.4 | 0.4 | |
| Absidia | isabellina | 4000 | | 0.9 | | | 0.8 | | | | | | | | | | |
| Mortierella | eleongata | 8183 | | | | | 0.1 | | | 0.1 | | 0.2 | | | | | |
| Mortierella | elegans | 8570 | | | | | 0.6 | 0.1 | | 0.1 | 0.1 | | 0.1 | | | | |
| Cunninghamella | caerulescens | 4441 | | | 7.1 | | 0.6 | | | | | | | | | | |
| Taphrina | wiesneri | 9242 | | 0.3 | | | 0.6 | | | | | | | | | | |
| Taphrina | anka | 7776 | | 1.1 | 11.6 | | 0.2 | | | 0.2 | 0.5 | 0.5 | | | | | |
| Monascus | albidus | 6540 | | 0.5 | | | 0.4 | | | | | | | | | | |
| Monascus | flammea | 4489 | | 1.1 | 24.9 | | 0.4 | | | | | | | | | | |
| Nectria | fujikuroi | 9628 | | 2.6 | 44.1 | | 1.2 | | | 0.6 | | 0.2 | | | | | |
| Giberella | globosum | 5268 | | | 7.1 | | 0.1 | | | 0.1 | | 0.1 | | 0.2 | | | |
| Chaetomium | crassa | 6347 | | | 0.3 | | | | | 0.1 | | | | | | | |
| Neurospora | candidum | 6067 | | | 7.1 | | 0.4 | | | | | | | | | | |
| Geotrichum | geophila | 4597 | | | 31.2 | | 0.8 | | 0.1 | 0.1 | 0.1 | | | | | | |
| Monilia | viride | 5425 | | 0.7 | 16.0 | | 1.0 | | 0.1 | | | | 0.1 | | | | |
| Trichoderma | clavatus | 4847 | | 1.2 | | | 0.7 | | | | 0.1 | | | | | | |
| Aspergillus | clavatus | 4045 | | | | | 0.6 | | | | 0.1 | | | | | | |
| Aspergillus | | 8606 | | | 22.4 | | | | | | | | | | | | |
| | | | | | | Fungi (2) | | | | | | | | | | | |
| Penicillium | digitatum | IFO 7758 | | | 1.0 | | | | 0.1 | 0.1 | 0.1 | | | | | | |
| Penicillium | digitatum | 9372 | | trace | 1394 | | | | | | | | | | | | |
| Paecilomyces | carcus | 8292 | | 1.1 | | | 0.2 | | | 0.2 | | 0.4 | | | | | |
| Paecilomyces | elegans | 6619 | | | 16.0 | | 1.0 | | 0.1 | 0.1 | | | | | | | |
| Gliocladium | aureum | 9055 | | 2.1 | | | 0.9 | | 0.1 | 0.7 | | | | | | | |
| Gliocladium | diligenscens | 7062 | | 0.1 | 9.8 | | 0.1 | | | 0.1 | | 0.6 | 0.1 | | | | |
| Sporotrichum | roseum | 7063 | | | 8.9 | | | 3.0 | | | 0.3 | | | | | | |
| Sporotrichum | aureum | 9381 | | 2.4 | | | 0.5 | | | | 0.5 | 0.5 | | | | | |
| Microsporum | gypseum | 5948 | | | 7.1 | | 0.2 | | 0.1 | 0.1 | | 0.2 | | | | | |
| Microsporum | cookei | 7862 | | 1.4 | 0.1 | | | | | | | | | | | | |

TABLE 5-continued

Formation of hydrocarbon mixtures by each strain
[Numerals in the Table show formation rates (nl/ml/hour)]

| Genera | Species | Strains | C₁ methane | ethane | C₂ ethylene | acetylene | C₃ propane | propylene | iso- butane | n- butane | 1- butene | iso- butene | trans-2- butene | cis-2- butene | C₅ iso- pentane | n- pentane | remarks |
|---|---|---|---|---|---|---|---|---|---|---|---|---|---|---|---|---|---|
| Tricophyton | mentagrophytes | 5466 | | 1.9 | 29.4 | | | | | | | 0.1 | | | | | |
| Cladosporium | resinae | 8588 | | | 11.6 | | | | | 0.1 | | 0.5 | | | | | |
| Syncephalastrum | racemosum | 4816 | | 1.3 | 38.2 | | | | | 0.1 | | 0.2 | | | | | |
| Phycomyces | nitens | 9422 | | | | | | | | 0.1 | | 0.3 | | | | | |
| Eupenicillium | lapidosum | 6100 | | 0.1 | 0.1 | | 0.1 | | | | | | | | | | |
| Eupenicillium | lapidosum | 9700 | | 0.1 | 0.1 | | 0.1 | 0.1 | | | | | | | | | |
| Eupenicillium | lapidosum | 9701 | | 0.1 | 0.1 | | 0.1 | 0.1 | | | | | | | | 0.1 | |
| | | | | | | Yeasts (1) | | | | | | | | | | | |
| Endomyces | geotrichum | IFO 9541 | | 0.2 | | | 1.0 | | | 0.1 | | 0.2 | | | | | |
| Endomyces | reessii | 1112 | | | | | 1.0 | 0.1 | | | 0.1 | | 0.6 | | | | |
| Endomyces | magnusii | 0110 | | 0.3 | 0.1 | | 0.5 | 1.2 | | | | | | | | 0.1 | |
| Schizosaccharomyces | octosporus | 0353 | 12.1 | | 0.3 | | 0.1 | | | | | 0.5 | | | | | |
| Schizosaccharomyces | pombe | 0340 | 11.4 | | 204.4 | | 0.1 | | | | | | | | | | |
| Saccharoyces | bailii | 0468 | | 0.6 | | | 0.2 | 0.1 | | | | | | | | | |
| Pichia | membranaefaciens | 0181 | | 0.2 | 0.7 | | 0.1 | | | | | | | | | | |
| Pichia | acaciae | 1681 | | 0.2 | 0.7 | | 0.1 | | 0.1 | 0.1 | 0.1 | 0.1 | | | | | |
| Pichia | besseyi | 1707 | | | | | 0.9 | | | 0.1 | | | | | | | |
| Pichia | farinosa | 0459 | | 0.1 | | | 0.9 | | | 0.2 | | | | | | | |
| Hansenula | capsulata | 0721 | | | | | 0.2 | 0.1 | | 0.1 | | | | | | | |
| Debaryomyces | nepalensis | 1428 | | 0.4 | 0.2 | | 0.1 | | 0.1 | | | 0.1 | | | | | |
| Saccaromycopsis | lipolytica | 1658 | | 0.1 | 0.6 | | 0.5 | | 0.1 | | | 0.1 | | 0.1 | | | |
| Saccaromycopsis | crataegensis | 1708 | | | 0.3 | | 0.4 | 0.1 | | | | 0.3 | | | | | |
| Saccaromycopsis | fiburigera | 1745 | | | | | 1.1 | | 0.2 | | | | | | | | |
| Rhodotorula | glutinis | 0697 | | 0.2 | 3.6 | | 0.7 | | 0.1 | | | | | | | | |
| Rhodotorula | glutinis | 1501 | | | 0.7 | | | 0.1 | | | | 1.7 | | | | | |
| Rhodotorula | minuta | 0387 | | | 0.2 | | 0.2 | | | | | 1.0 | | | | | |
| Rhodotorula | minuta | 1435 | | | | | | 0.1 | | | | 0.9 | | | | | |
| Rhodotorula | minuta var. texensis | 0879 | | | 0.1 | | | | | | | | | | | | |
| Rhodotorula | minuta var. texensis | 0932 | | | 0.2 | | 0.2 | | | | | 1.6 | | 0.1 | | | |
| Rhodotorula | minuta var. texensis | 1006 | | | | | 0.1 | | | 0.1 | | 1.1 | | | | | |
| Rhodotorula | minuta var. texensis | 1102 | | | 0.2 | | 0.2 | | | 0.1 | | 4.3 | | 0.1 | 0.1 | 0.7 | |
| Rhodotorula | marina | 1421 | | | 0.1 | | 0.2 | | 0.1 | | | 2.7 | | | | | |
| Sporobolomyces | salmonicolor | 0374 | | | 0.9 | | 0.4 | 0.1 | | 0.1 | 0.1 | 0.2 | | | | | |
| Sporobolomyces | pararoseus | 0376 | | 0.5 | 12.2 | | 0.3 | | 0.1 | | | 0.3 | | | | | |
| Candida | albicans | 1060 | | 1.4 | 5.3 | | 0.3 | 0.2 | | | | | | | | | |
| Candida | butyri | 1571 | | | | | 1.2 | | | | 0.1 | 0.2 | | | | | |
| Candida | guilliermodii | 0454 | | | 0.2 | | 0.5 | | | 0.1 | | | | | | | |
| Brettanomyces | bruxellensis | 0628 | | 15.8 | 10.8 | | 0.2 | | | 0.1 | | | | | | | |
| Brettanomyces | intermedius | 1587 | | 0.6 | | | 0.1 | | | | | 0.1 | | | | | |
| | | | | | | Yeasts (2) | | | | | | | | | | | |
| Cryptococcus | albidus | IFO 0378 | | 0.2 | | | 6.5 | 0.1 | 0.1 | 0.1 | | | | | | | |

TABLE 5-continued

Formation of hydrocarbon mixtures by each strain
[Numerals in the Table show formation rates (nl/ml/hour)]

| Genera | Species | Strains | C₁ methane | C₂ ethane | C₂ ethylene | C₂ acetylene | C₃ propane | C₃ propylene | C₄ iso-butane | C₄ n-butane | C₄ 1-butene | C₄ iso-butene | C₄ trans-2-butene | C₄ cis-2-butene | C₅ iso-pentane | C₅ n-pentane | remarks |
|---|---|---|---|---|---|---|---|---|---|---|---|---|---|---|---|---|---|
| Cryptococcus | albidus | 0434 | | 0.1 | 0.6 | | 0.3 | 0.3 | | 0.3 | | | | | | | |
| Cryptococcus | albidus | 0939 | | 0.3 | 4.2 | | 0.1 | | | 0.1 | | | | | | | |
| Cryptococcus | albidus | 1044 | | | 0.2 | | | | | | | 0.1 | | | | | |
| Cryptococcus | albidus | 1320 | | 0.1 | 1.3 | | 1.4 | 0.1 | 0.4 | 1.9 | 0.3 | 4.4 | | | | | |
| Cryptococcus | flavus | 0407 | | 1.0 | 1.0 | | 0.1 | 0.4 | 0.8 | 0.1 | 0.2 | | | | | | |
| Cryptococcus | laurentii var. flavescens | 0384 | | 3.1 | 54.6 | | 0.9 | | 0.1 | 0.1 | | 0.1 | | 0.7 | | | |
| Cryptococcus | luteolus | 0441 | | 0.1 | 0.6 | | 0.3 | 0.2 | 0.1 | 0.2 | 0.1 | | | | | | |
| Saccharomyces | sp. | 2363 | | | | | 0.3 | 0.2 | | | | 0.2 | | | | | |
| Saccharomyces | sp. | 2226 | | 0.1 | | | 0.5 | 0.1 | | | | | | | | | |
| Saccharomyces | sp. | 2112 | | | | | 0.5 | 0.1 | | | 0.1 | | | | | | |
| Saccharomyces | sp. | 2115 | | 0.2 | | | 0.5 | | | 0.1 | | 0.1 | | | | | |
| Saccharomyces | sp. | 2342 | | | | | 1.3 | | | | | | | | | | |
| Saccharomyces | sp. | 2343 | | | | | 0.1 | | | | | | | | | | |
| Saccharomyces | sp. | 2344 | | 0.1 | | | 0.2 | 0.1 | | 0.1 | | 0.2 | | | | | |
| Saccharomyces | sp. | 2345 | | | | | 0.4 | | | | | | | | | | |
| Saccharomyces | sp. | 2346 | | 0.4 | | | 1.1 | 0.1 | 0.1 | | | | | | | | |
| Saccharomyces | sp. | 2347 | | | | 0.2 | 0.1 | 0.1 | | | | | | | | | |
| Saccharomyces | sp. | 2376 | | | | | 0.1 | 0.2 | | | | | | | | | |
| Bacteria | | | | | | | | | | | | | | | | | |
| Acetobacter | aceti | IFO 3281 | | 0.1 | 0.2 | | 0.2 | | | | | | | | | | |
| Bacillus | circulans | 3329 | | | 0.4 | | 0.1 | 0.1 | | 0.1 | 0.2 | | 0.2 | | | | |
| Bacillus | coagulans | 3557 | | | | | 0.3 | 0.2 | 0.1 | 0.2 | 0.4 | | | | | | |
| Bacillus | pumilus | 3813 | | | | | 0.1 | | | | | | | | | | |
| Bacillus | subtilis | 3023 | | 0.2 | | | 0.1 | 0.1 | 0.1 | 0.1 | 0.2 | 0.1 | | | | | |
| Brevibacterium | ammoniagenes | ATCC 6872 | | | 0.9 | | 8.6 | 0.1 | | | 0.2 | 0.1 | 0.2 | | | | |
| Brevibacterium | lactofermentum | ATCC 13655 | | | 0.6 | | 0.2 | 0.2 | 0.1 | | 0.2 | 0.1 | 0.2 | | | | |
| Corynebacterium | aquaticum | IFO 12154 | | 0.1 | 1.8 | | 0.3 | 0.2 | | 0.2 | | | | | | | |
| Corynebacterium | fascians | 12077 | | | 1.5 | | | | 0.1 | 0.7 | | | 0.2 | | | | |
| Corynebacterium | paurometabolum | 12160 | | 1.0 | 3.0 | | | | | | | | | | | | |
| Flavobacterium | capsulatum | 12533 | | | 2.0 | | 0.7 | 0.2 | | | | | | | | | |
| Klebsiella | pneumoniae | 3317 | | | 0.7 | | | | | | | | | | | | |
| Micrococcus | luteus | 3064 | | | 0.1 | | 0.2 | 0.2 | 0.1 | | | | | | | | |
| Micrococcus | roseus | 3764 | | | 9.0 | | 2.3 | | | | | | | | | | |
| Mycoplana | dimorpha | 13291 | | 1.5 | 0.1 | | 0.1 | | | | | | | | | | |
| Paracoccus | denitrificans | 12442 | | | 0.2 | | 0.2 | 0.2 | 0.1 | 0.1 | 0.2 | | 0.1 | | | | |
| Proteus | mirabilis | 3849 | | | 0.2 | | 2.2 | 0.3 | 0.1 | 0.1 | | | 0.2 | | | | |
| Pseudomonas | aeruginosa | 3445 | | 0.1 | 0.8 | | 0.4 | | 0.1 | 0.1 | | | 0.1 | | | | |
| Pseudomonas | putida | 3738 | | | 0.5 | | 2.3 | 0.2 | 0.1 | 0.1 | | | 0.2 | | | | |
| Pseudomonas | stutzeri | 3773 | | 3.1 | 0.1 | | 2.3 | 0.2 | 0.1 | 0.1 | | | 0.1 | | | | |
| Salmonella | typhimurium | 12529 | | | | | 0.1 | 0.2 | | | | 0.1 | | | | | |
| Serratia | marcescens | 12648 | | | 0.4 | | 0.1 | 0.1 | 0.1 | 0.1 | | | 0.2 | | | | |
| Actinomycetes | | | | | | | | | | | | | | | | | |

TABLE 5-continued

Formation of hydrocarbon mixtures by each strain
[Numerals in the Table show formation rates (nl/ml/hour)]

| Genera | Species | Strains | C₁ | | C₂ | | C₃ | | C₄ | | | | | | C₅ | | remarks |
|---|---|---|---|---|---|---|---|---|---|---|---|---|---|---|---|---|---|
| | | | methane | ethane | ethylene | acetylene | propane | propylene | iso-butane | n-butane | 1-butene | iso-butene | trans-2-butene | cis-2-butene | iso-pentane | n-pentane | |
| Streptomyces | flaveolus | IFO 3408 | | | | | | | | 0.4 | | | 0.2 | | | | |
| Streptomyces | fradiae | 3360 | | 0.1 | | | 0.2 | | 0.2 | 0.3 | | | | | | | |
| Streptomyces | griseus | 3102 | | | 0.2 | | 1.2 | 0.1 | 0.3 | 0.2 | | | | | | | |
| Streptomyces | lavendulae | 3145 | | 0.5 | 0.2 | | 1.2 | 0.1 | 0.2 | 0.2 | | | 0.2 | | | | |
| Streptomyces | lavendulae | 13709 | | | 0.2 | | 0.2 | 0.3 | | 0.1 | | | 0.4 | | | | |
| Streptomyces | viridochromogenes | 3113 | | | 0.2 | | 0.2 | 0.1 | | | | | | | | | |
| Streptomyces | regensis | 13448 | | | | | 0.2 | 0.1 | 0.1 | | | | | | | | |
| Actinomyces | vulgaris | 13107 | | | 0.3 | | 0.2 | 0.1 | | | | | | | | | |
| Intrasporangium | calvum | 12989 | | | | | 0.3 | | 0.2 | 0.1 | | | | | | | |

EXAMPLE 2

The two strains of *Rhodotorula minuta* var. texensis IFO-1102 and *Rhizopus japanicus* IFO-4758 were cultivated on the slants of agar (1.5 w/v %)-NB medium indicated in Table 1, and sterile distilled water was aseptically added to the cultures to give cell suspensions.

Five hundred ml of the media for yeasts and the chemically defined media for fungi indicated in Table 1 was added to 3 liter capacity Sakaguchi flask, respectively and after steam sterilization by autoclaving at 120° C. for 15 minutes and cooling, the above cell suspensions were inoculated to each flask. The preculture of the yeast was conducted at 25° C. for 2 days and that of the fungus at 25° C. for 3 days, using a reciprocating shaker.

Jar fermentors of 14 liter capacity were charged with 10 liters of the NB media for yeasts or the chemically defined media (provided that 1 g/l of L-cystine was added) for fungi indicated in Table 1, respectively. After steam sterilization under pressure at 120° C. for 20 minutes and cooling, the above pre-cultures were inoculated to each jar fermentor. The fermentation of the yeast was conducted at 25° C. for 3 days and that of the fungus at 25° C. for 4 days, under aeration with sterile air at $0.1^{VVM}$ and at 200 to 300 r.p.m. (the r.p.m. was adjusted according to the degree of foaming).

Throughout the fermentation period, the gases discharged from each jar fermentor were independently passed through a 10% NaOH vessel, a washing vessel and a moisture separating vessel; followed by serial passage through Jeoram® A-3 and Jeoram® F-9 (geolite products of Toyo Soda Manufacturing Co., Ltd., Japan) columns and the hydrocarbons adsorbed on Jeoram F-9 were desorbed and recovered under vaccum saction.

The amounts of hydrocarbon mixtures thus obtained were 0.1 mg of ethylene, 0.1 mg of propane, 0.1 mg of n-butane, 3.8 mg of isobutene, 0.1 mg of isopentane and 0.1 mg of n-pentane with *Rhodotorula minuta;* and 2.3 mg of propane, 0.7 mg of n-butane, 4.3 mg of isopentane and 8.8 mg of n-pentane with *Rhizopus japanicus.*

We claim:

1. A method for producing a hydrocarbon mixture which comprises cultivating aerobically a strain of microorganism capable of producing simultaneously at least two kinds of saturated or unsaturated $C_2$–$C_5$ hydrocarbons in a water-containing medium to thereby cause the formation of said hydrocarbons in the liquid phase or/and the gaseous ambience of the medium, recovering said hydrocarbons from said liquid or/and gaseous ambience, and separating said hydrocarbons.

2. A method according to claim 1 wherein an increasing yield of isobutene is formed by adding L-leucine, or L-leucine and a benzene compound having a carboxyl group to the medium.

3. A method according to claim 1 wherein an increased yield of trans-2-butene and cis-2-butene are formed by adding L-isoleucine, or L-isoleucine and L-phenylalanine to the medium.

4. A method according to claim 1 wherein an increased yield of ethylene is formed by adding L-methionine to the medium.

5. A method according to claim 1 wherein an increased yield of saturated hydrocarbon is formed by adding L-cysteine to the medium.

6. A method according to claim 1 wherein the strain is a fungus or a mutant thereof belonging to Saprolegenia, Phytophthola, Mucor, Rhizopus, Absidia, Mortierella, Cunninghamella, Taphrina, Monascus, Nectria, Gibberella, Chaetomium, Neurospora, Geotrichum, Monilia, Tricoderma, Aspergillus, Penicillium, Paecilomyces, Glyocladium, Sporotrichum, Microsporum, Trichophyton, Cladosporium, Syncephalastrum, Phycomyces or Eupenicillium; a yeast or a mutant thereof belonging to Endomyces, Shizosaccharomyces, Saccharomyces, Pichia, Hansenula, Dabaryomyces, Saccharomycopsis, Rhodotorula, Sporobolomyces, Cryptococcus, Candida or Brettanomyces; a bacteria or a mutant thereof belonging to Bacillus, Brevibacterium, Corynebacterium, Flavobacterium, Klebsiella, Micrococcus, Mycoplana, Paracoccus, Proteus, Pseudomonas, Salmonella, Serratia or Acetobacter; or an actinomycetes or a mutant thereof belonging to Streptomyces, Actinomyces or Intrasporangium.

* * * * *